US012594374B2

(12) United States Patent
Tüysüz et al.

(10) Patent No.: US 12,594,374 B2
(45) Date of Patent: Apr. 7, 2026

(54) STACKABLE MANIFOLDS FOR MEDICAL FLUIDS

(71) Applicant: Asset Medical, Inc., San Diego, CA (US)

(72) Inventors: Mehmet Tüysüz, Mugla (TR); Ahmet Reha Basaran, Balikesir (TR); Saulius Umbrasas, San Diego, CA (US)

(73) Assignee: Asset Medical, Inc., San Diego, CA (US)

( * ) Notice: Subject to any disclaimer, the term of this patent is extended or adjusted under 35 U.S.C. 154(b) by 0 days.

(21) Appl. No.: 18/606,471

(22) Filed: Mar. 15, 2024

(65) Prior Publication Data

US 2025/0288736 A1    Sep. 18, 2025

(51) Int. Cl.
*A61M 5/14*        (2006.01)
*A61M 39/10*      (2006.01)
*A61M 39/24*      (2006.01)

(52) U.S. Cl.
CPC ........ *A61M 5/1408* (2013.01); *A61M 5/1413* (2013.01); *A61M 39/1011* (2013.01); *A61M 39/24* (2013.01)

(58) Field of Classification Search
CPC .......... A61M 2039/1088; A61M 39/10; A61M 5/1408; A61M 5/1413; A61M 39/223; A61M 2039/1083; Y10S 285/913; Y10S 285/918; Y10S 285/921
See application file for complete search history.

(56) References Cited

U.S. PATENT DOCUMENTS

| | | | | |
|---|---|---|---|---|
| 803,127 | A | * | 10/1905 | Palmer .................... F16L 47/04 |
| | | | | 285/402 |
| 980,677 | A | * | 1/1911 | Rhoads ................. F16L 37/252 |
| | | | | 285/86 |
| 1,873,304 | A | * | 8/1932 | De Mooy ............... F16L 37/23 |
| | | | | 285/277 |
| 2,764,978 | A | * | 10/1956 | Everett ................. A61M 5/347 |
| | | | | 604/242 |
| 2,902,995 | A | * | 9/1959 | Loper ................... A61M 5/348 |
| | | | | D24/114 |
| 3,834,372 | A | * | 9/1974 | Turney ................. F16K 11/085 |
| | | | | 600/561 |
| 4,040,421 | A | * | 8/1977 | Young ............... A61M 25/0014 |
| | | | | D24/114 |
| 4,211,439 | A | * | 7/1980 | Moldestad ............ F16L 37/113 |
| | | | | 285/376 |
| 4,275,907 | A | * | 6/1981 | Hunt ..................... F16L 37/133 |
| | | | | 285/330 |

(Continued)

FOREIGN PATENT DOCUMENTS

DE        202016104462 U1 * 11/2017   ............ A61M 39/10

*Primary Examiner* — Scott J Medway
(74) *Attorney, Agent, or Firm* — Carter, DeLuca & Farrell LLP; George Likourezos

(57)        ABSTRACT
A manifold including two or more connectors, or a manifold comprising a first connector and a second connector for communication of medical fluids. The manifold is constituted by engaging a first-gender first end of a connector to a complementarily shaped second-gender second end of a further connector; or the manifold is constituted by engaging a first-gender first end of the first connector to a complementarily shaped second-gender second end of the second connector.

15 Claims, 11 Drawing Sheets

(56) References Cited

U.S. PATENT DOCUMENTS

| 4,447,230 | A | * | 5/1984 | Gula | A61M 5/1408 |
| | | | | | 604/122 |
| D275,233 | S | * | 8/1984 | DeVroom | D24/129 |
| 4,585,435 | A | * | 4/1986 | Vaillancourt | A61M 5/158 |
| | | | | | D24/114 |
| 4,734,091 | A | * | 3/1988 | Boyle | A61M 3/0208 |
| | | | | | 604/521 |
| 4,790,567 | A | * | 12/1988 | Kawano | A61M 39/10 |
| | | | | | 285/914 |
| 5,104,157 | A | * | 4/1992 | Bahner | F16L 37/084 |
| | | | | | 285/307 |
| 5,113,571 | A | * | 5/1992 | Manska | A61M 39/10 |
| | | | | | 285/332 |
| 5,190,525 | A | * | 3/1993 | Oswald | A61M 5/1408 |
| | | | | | 604/83 |
| 5,312,377 | A | * | 5/1994 | Dalton | A61M 39/10 |
| | | | | | 285/332 |
| 5,356,375 | A | * | 10/1994 | Higley | A61M 5/36 |
| | | | | | 604/35 |
| 5,460,204 | A | * | 10/1995 | Rossi | A61M 5/1408 |
| | | | | | 137/271 |
| 5,624,638 | A | * | 4/1997 | Negrotti | G09B 19/0069 |
| | | | | | 206/229 |
| 5,772,643 | A | * | 6/1998 | Howell | A61M 25/02 |
| | | | | | 138/155 |
| 6,099,511 | A | * | 8/2000 | Devos | A61M 5/1408 |
| | | | | | 604/82 |
| 6,290,682 | B1 | * | 9/2001 | Myers | F16K 7/17 |
| | | | | | 604/247 |
| 6,367,507 | B1 | * | 4/2002 | Legeai | F16L 41/16 |
| | | | | | 137/884 |
| 6,508,791 | B1 | * | 1/2003 | Guerrero | A61M 5/1408 |
| | | | | | 604/247 |
| 6,752,791 | B2 | * | 6/2004 | Murphy | A61B 17/8819 |
| | | | | | 604/173 |
| 6,880,808 | B2 | * | 4/2005 | McPeak | F16K 5/045 |
| | | | | | 251/312 |
| 7,044,937 | B1 | * | 5/2006 | Kirwan | A61B 17/00491 |
| | | | | | 604/167.03 |
| 8,016,809 | B2 | * | 9/2011 | Zinger | A61J 1/2096 |
| | | | | | 604/414 |
| 8,777,931 | B2 | * | 7/2014 | Davis | A61M 39/10 |
| | | | | | 285/332 |
| 8,945,091 | B2 | * | 2/2015 | Williams | A61M 39/10 |
| | | | | | 285/305 |
| 9,109,724 | B2 | * | 8/2015 | Meissner | F16L 3/1091 |
| 9,259,527 | B2 | * | 2/2016 | Spohn | A61M 5/007 |
| 9,468,709 | B2 | * | 10/2016 | Shippert | A61M 1/89 |
| 9,895,527 | B2 | * | 2/2018 | Spohn | A61M 39/24 |
| 10,406,342 | B2 | * | 9/2019 | Ueda | A61M 39/1011 |
| 10,441,775 | B2 | * | 10/2019 | Schriver | A61M 5/16827 |
| 11,801,376 | B2 | * | 10/2023 | Knight | A61M 39/223 |
| 2003/0184090 | A1 | * | 10/2003 | Guala | A61M 39/1011 |
| | | | | | 285/332 |
| 2004/0221904 | A1 | * | 11/2004 | Usher | A61M 39/24 |
| | | | | | 137/837 |
| 2006/0149189 | A1 | * | 7/2006 | Diamond | A61M 5/007 |
| | | | | | 604/246 |
| 2008/0058727 | A1 | * | 3/2008 | Domash | A61M 39/12 |
| | | | | | 604/174 |
| 2008/0103484 | A1 | * | 5/2008 | Hishikawa | A61M 39/26 |
| | | | | | 604/533 |
| 2009/0275829 | A1 | * | 11/2009 | Agarwal | A61M 31/005 |
| | | | | | 600/433 |
| 2009/0306621 | A1 | * | 12/2009 | Thome, Jr. | A61M 39/223 |
| | | | | | 604/82 |
| 2010/0168718 | A1 | * | 7/2010 | Bellisario | A61M 1/3661 |
| | | | | | 604/533 |
| 2011/0034899 | A1 | * | 2/2011 | Thome, Jr. | A61M 39/18 |
| | | | | | 604/407 |
| 2014/0034169 | A1 | * | 2/2014 | Harton | A61M 5/16827 |
| | | | | | 137/798 |
| 2014/0107480 | A1 | * | 4/2014 | Spohn | A61M 5/007 |
| | | | | | 600/432 |
| 2014/0261758 | A1 | * | 9/2014 | Wlodarczyk | A61M 5/14566 |
| | | | | | 285/305 |
| 2015/0045772 | A1 | * | 2/2015 | Reichert | A61M 5/1413 |
| | | | | | 604/507 |
| 2015/0119709 | A1 | * | 4/2015 | Coolidge | A61M 5/1723 |
| | | | | | 600/432 |
| 2018/0008812 | A1 | * | 1/2018 | Roxas | A61M 1/367 |
| 2018/0177978 | A1 | * | 6/2018 | Spivey | A61B 17/00491 |
| 2019/0009072 | A1 | * | 1/2019 | Schedler | A61M 39/1011 |
| 2019/0107516 | A1 | * | 4/2019 | Shirkhan | G01N 30/6047 |
| 2020/0306462 | A1 | * | 10/2020 | Leung | A61M 5/3148 |
| 2021/0106804 | A1 | * | 4/2021 | McArthur | A61M 39/105 |
| 2023/0001176 | A1 | * | 1/2023 | Otto | B29C 66/5344 |
| 2023/0070065 | A1 | * | 3/2023 | Callahan | A61M 39/10 |
| 2023/0338723 | A1 | * | 10/2023 | Sealfon | A61M 5/1408 |
| 2024/0198077 | A1 | * | 6/2024 | Dowell | A61M 39/22 |

* cited by examiner

10

11        12

10

11        12

100

20        24        25        10        25        24        20

20        26        26

100

10        26

12        11        200

100

10        26

12        11        200

100

100    100    100    100

100

151

31        151        31

31

151

30

31        31

30        30

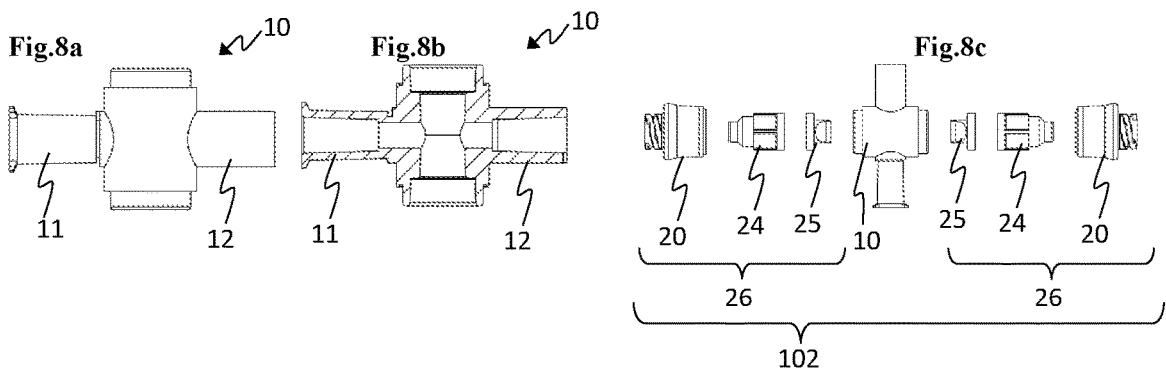
Fig.8a    10    11   12
Fig.8b    10    11   12
Fig.8c    20   24   25   10   25   24   20    26   26   102
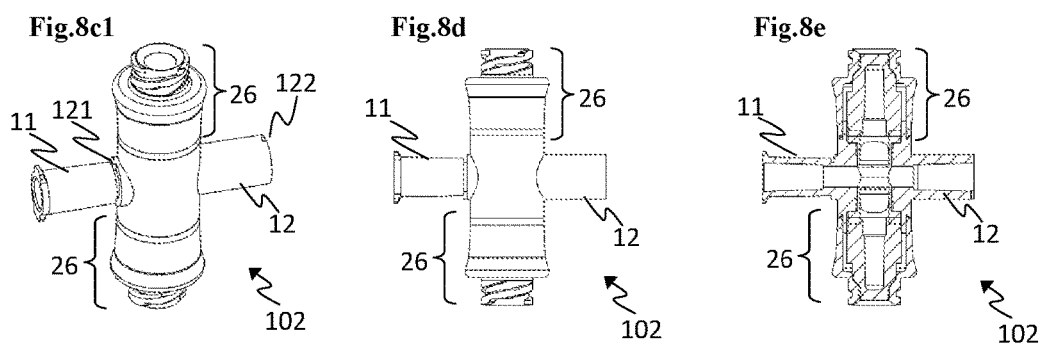
Fig.8c1   11   121   26   122   12   26   102
Fig.8d   11   26   12   26   102
Fig.8e   11   26   12   26   102
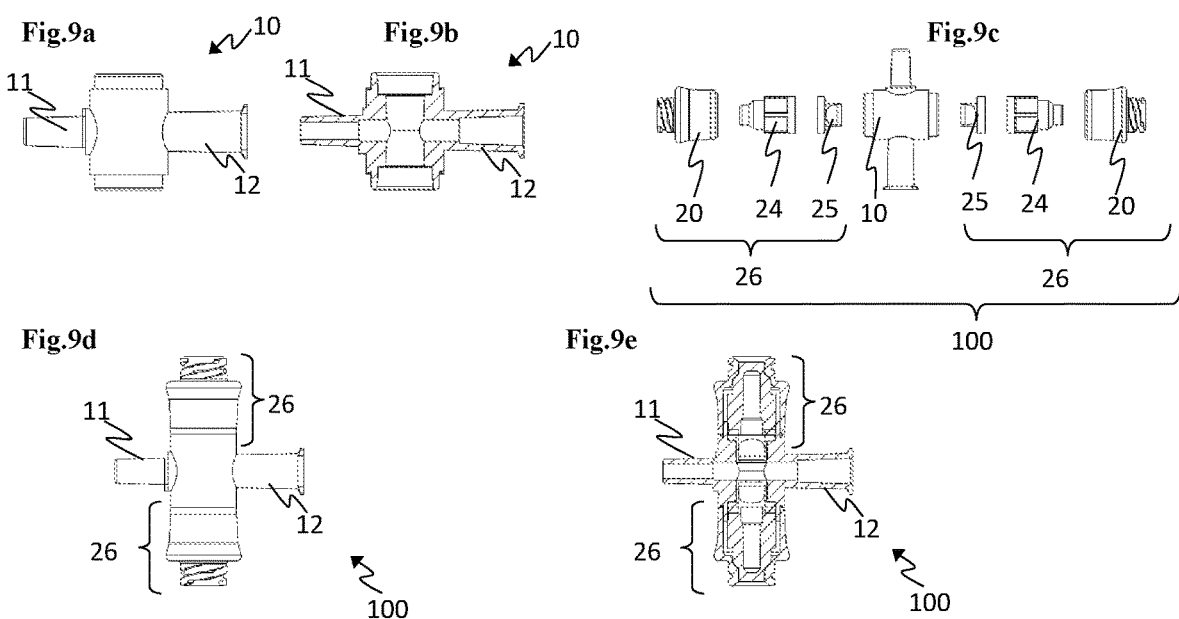
Fig.9a   10   11   12
Fig.9b   11   10   12
Fig.9c   20   24   25   10   25   24   20    26   26   100
Fig.9d   11   26   12   26   100
Fig.9e   11   26   12   26   100

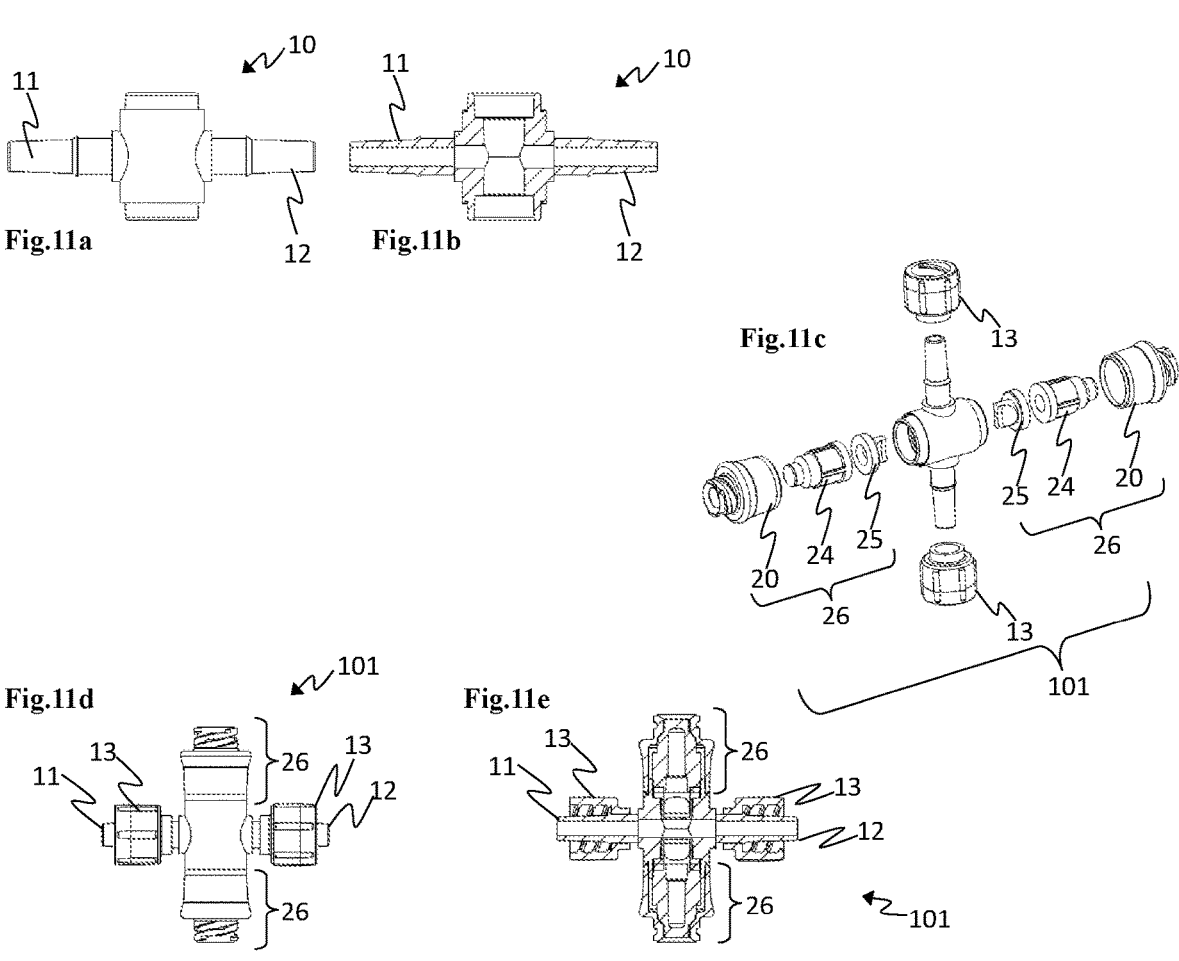
Fig.11a
Fig.11b
Fig.11c
Fig.11d
Fig.11e
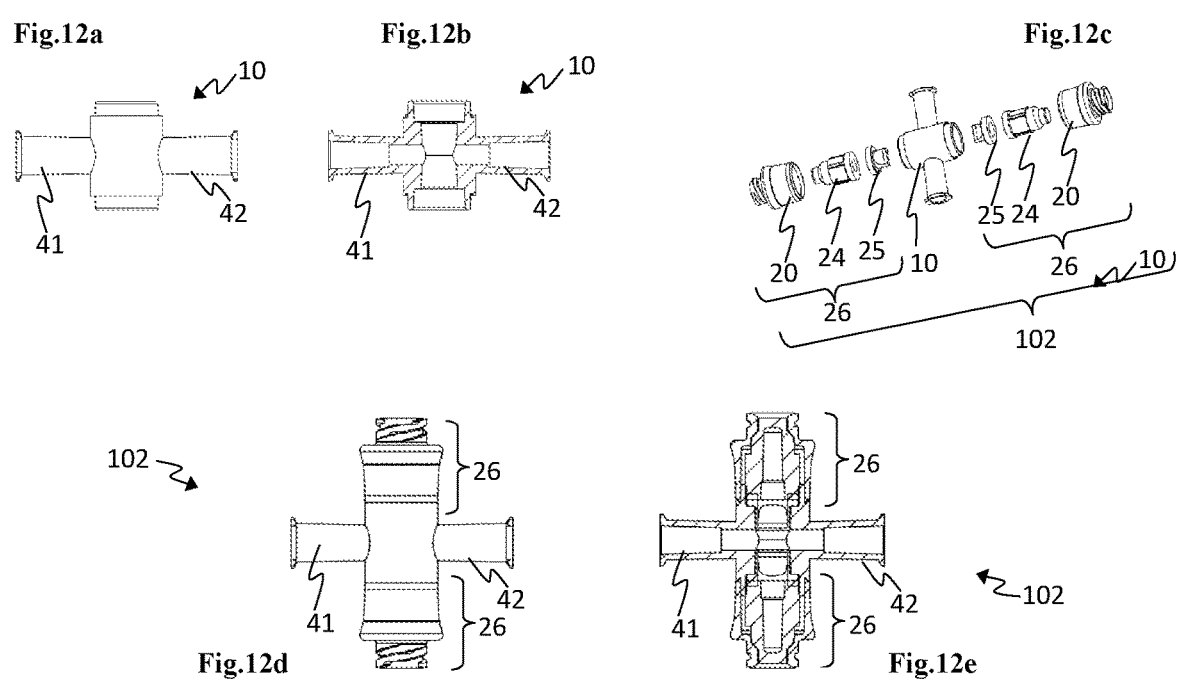
Fig.12a
Fig.12b
Fig.12c
Fig.12d
Fig.12e Fig.13a
101                   102                   101
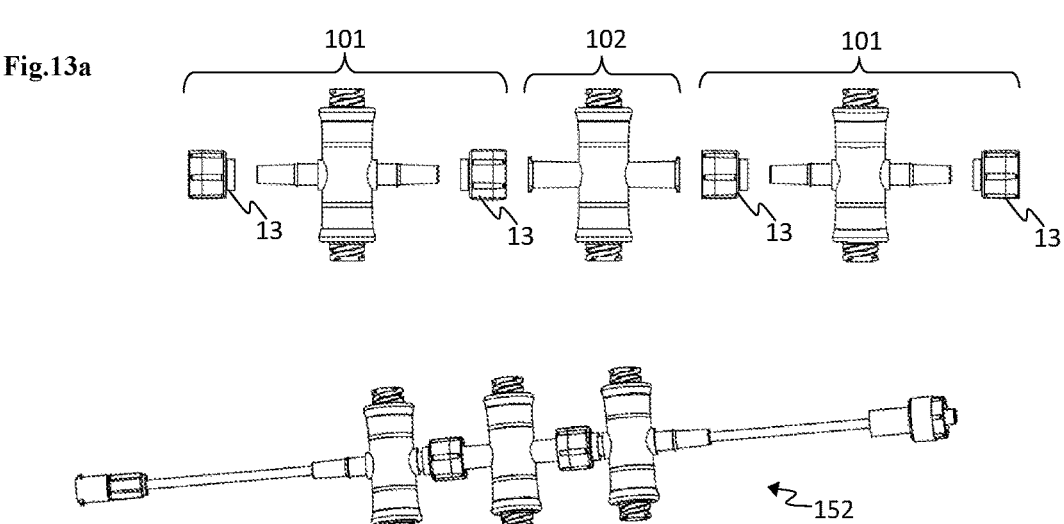
13                13                13                13
Fig.13b
152
Fig.14a
152
152
Fig.14b
152
Fig.14c
152
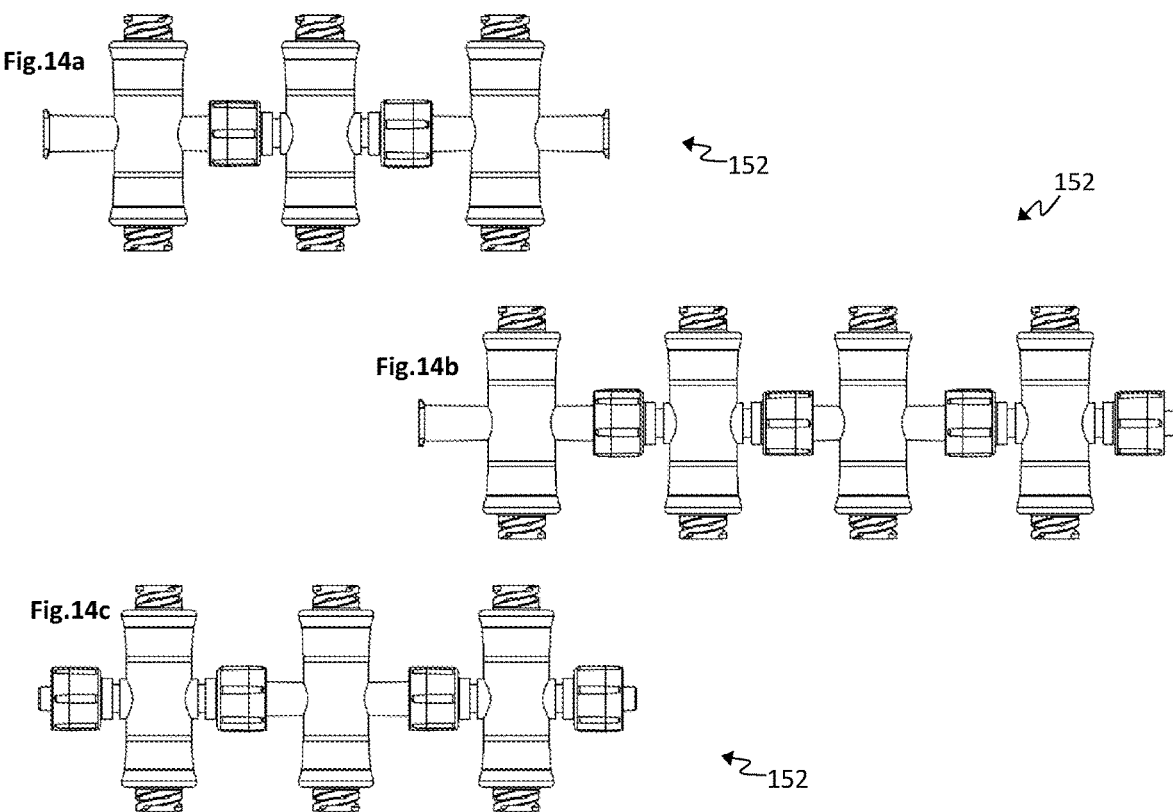

Fig.15a
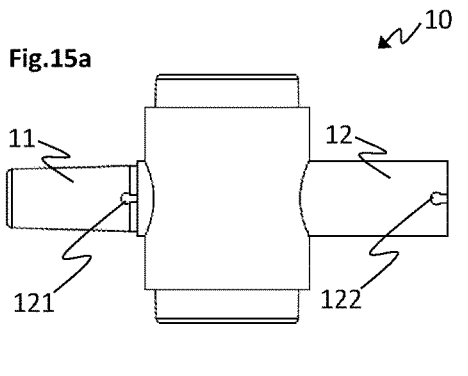
Fig.15b
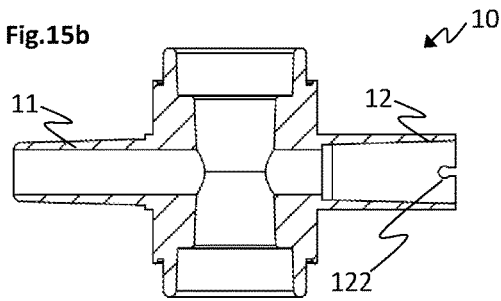
Fig.15c
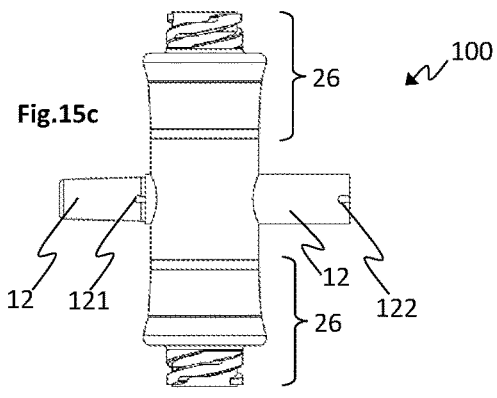
Fig.15d
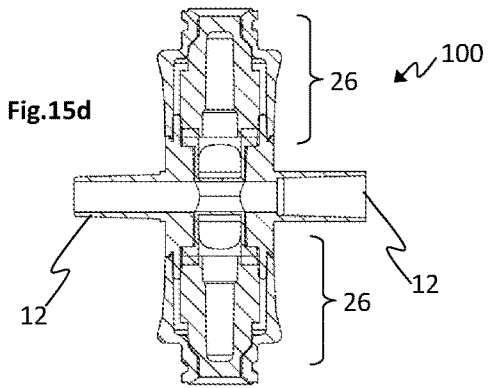
Fig.15e
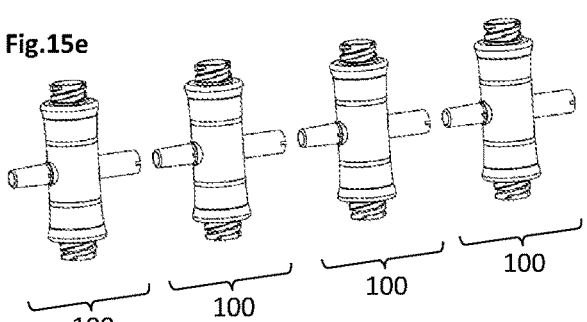
Fig.15f
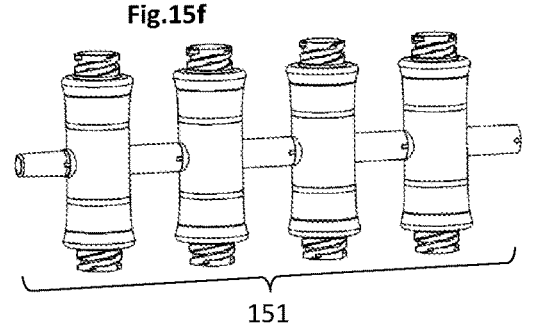
Fig.15g
Fig.15h
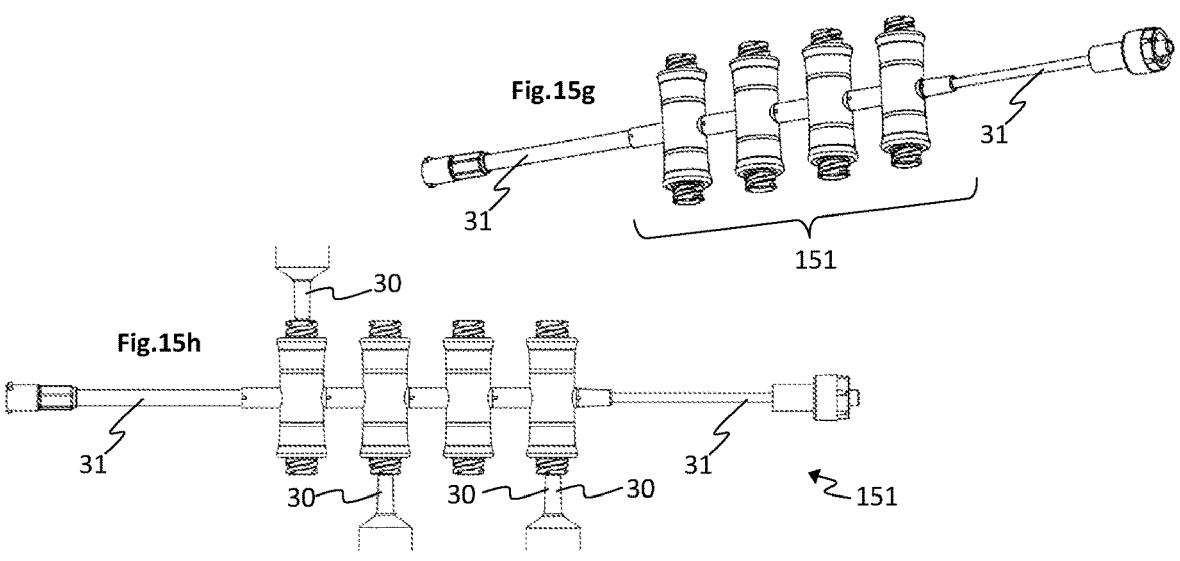

STACKABLE MANIFOLDS FOR MEDICAL FLUIDS

TECHNICAL FIELD

The present application relates to manifolds for communication of medical fluids.

BACKGROUND

Manifolds for communication of medical fluids to a patient generally include a rigid body that is provided with a number of valves at pre-determined, fixed positions and orientations. Such structure provides a fixed size, weight and internal volume that are proportional to the number of ports. It is not always possible to arrange a balanced distribution of combined weight, when a number of means for administering medical fluids such as needleless injectors are attached to the valves of such manifolds. The only way to alter the number of valves on this type of manifold is addition of a further one or more of such manifolds, but decreasing the number of valves is not possible. That is, in the case where a necessary number of valves for a specific treatment are lower than that are already present on the manifold, the manifold will have an excessive extent of priming volume, which is not desired. On the other hand, in the case where the number of valves present on the manifold is short for a specific treatment, and if a further one of same manifolds is added to the system, which would also correspond to an undesired increase in priming volume.

US 20150045772 A1 discloses several fixed-weight and fixed-size manifold embodiments that are provided with a number of valves at pre-determined, fixed positions and orientations.

On the other hand, design flexibility can be achieved by connecting compact (e.g., single-valve) bodies with one another via non-rigid medical tubings. This allows arrangement of different numbers of valves. Yet, due to the non-rigid nature of medical tubing, the resulting structure would bend or undergo torsion when in use. Accordingly, the resulting structure would not be able to maintain its general form that might be aimed at assembling stage. Furthermore, medical tubings in-between consecutive bodies would increase the priming volume to undesired extents and also result in a structure that dangles when in use. Even further, number of parts to be handled at assembling, that is, bodies to be consecutively arranged, and tubing pieces in-between the bodies, is inevitably high due to the requirement of said tubing pieces. This corresponds to a cumbersome assembling process, in addition to all of the disadvantages mentioned above.

SUMMARY

In various embodiments, the present disclosure discloses a medical manifold assembly comprising two or more connectors for use in a fluid pathway, that overcomes the shortcomings in the prior art. A further object of the present application is to propose medical manifold embodiments that provide easy and flexible assembly at preparation for conduction of medical fluids through two or more ports thereon, when interconnected or stacked together to form the medical manifold assembly. An even further object of the present application is to propose medical manifold assembly embodiments formed from two or more connectors stacked to one another, with a minimized or flexibly arrangeable priming volume, weight and size. These objects are achieved by the set of features that constitute the appended independent claims.

Any manifold assemblies within the context of the present disclosure can be referred to as manifold.

In a first aspect, the present application proposes a manifold for communication of medical fluids to or from a fluid pathway. The manifold comprises two or more connectors that are engaged (that is, interconnected, in other words, stacked) together. The following can be considered to apply to each of the two or more connectors:

the connector comprises a connector body; the connector body comprises a first end and a second end on a first axis; the first end and second end can be considered as an inlet and outlet for the medical fluid; the connector body is arranged to define an inner volume as a conduit for a stream of the medical fluid, to flow along a flow direction between a first end and second end; the connector body is provided with one or more ports in fluid communication with said inner volume in-between the first end and second end; the first end is in the form of a first type of a medical fluid communication interface geometry, and the second end is in the form of a second type of a medical fluid communication interface geometry that is different from the first type and geometrically complementary to said first type.

In a possible embodiment according to the first aspect; the first end can have a male fluid communication interface geometry and the second end can be a female fluid communication interface geometry; or the first end can be a female fluid communication interface geometry and the second end can have a male fluid communication interface geometry. The first end can have a male luer slip fluid communication interface geometry or a male luer lock fluid communication interface geometry, and the second end can be a female luer slip fluid communication interface geometry or a female luer lock fluid communication interface geometry; or the first end can be a female luer slip fluid communication interface geometry or a female luer lock fluid communication interface geometry, and the second end can have a male luer slip fluid communication interface geometry or a male luer lock fluid communication interface geometry.

In a possible embodiment according to the first aspect; the connector can be provided with one or more first anti-rotation means and one or more second anti-rotation means arranged to geometrically match the one or more first anti-rotation means, for stabilizing the manifold against rotating around the first axis relative to an identical, further connector, when the first end of the connector is engaged to the second end of the further connector.

In the manifold according to the first aspect, two or more connectors are stacked with one another, such that the first end of one of the connectors is engaged to the second end of another one of said connectors.

In a second aspect, the present disclosure proposes a manifold comprising one or more first connectors and one or more second connectors that are engaged to one another. The first connectors and second connectors can be considered to be alternatingly arrangeable by having complementary, single-gender structures. Accordingly, both of the first connector and second connector comprise a connector body having a first end and second end on a first axis, as an inlet and outlet for the medical fluid. The connector body can be considered as arranged for defining an inner volume as a conduit for a stream of medical fluid to flow along a flow direction between the first end and second end. The connector body is provided with one or more ports in fluid communication with said inner volume in-between the first end and second end. In the first connector, the first end and the second end are in the form of a first type of a medical fluid communication interface geometry. In the second connector, the first end and the second end are in the form of a second type of a medical fluid communication interface geometry that is different from the first type and geometrically complementary to said first type.

In a possible embodiment, the first end and the second end in the one or more first connectors have male fluid communication interface geometries, and the first end and the second end in the one or more second connectors have female fluid communication interface geometries. In a possible embodiment, the first end and the second end in the one or more first connectors have male luer slip fluid communication interface geometries, and the first end and the second end in the one or more second connectors have female luer slip fluid communication interface geometries. In another possible embodiment, the first end and the second end in the one or more first connectors have male luer lock fluid communication interface geometries, and the first end and the second end in the one or more second connectors have female luer lock fluid communication interface geometries.

In a possible embodiment, the one or more first connectors and the one or more second connectors can be provided with one or more first anti-rotation means and one or more second anti-rotation means that are arranged to geometrically match the one or more first anti-rotation means. The first anti-rotation means and second anti-rotation means are arranged for stabilizing the first connector against rotating around the first axis relative to the second connector, when the first connector and the second connector are engaged to one another.

The manifold according to the second aspect comprises one or more of the first connectors and one or more of the second connectors according to any of the possible embodiments. In the manifold, the one or more of the first connectors are stacked with the one or more of the second connectors, such that such that the first end of the one or more first connectors is engaged to the second end of the one or more second connectors.

In a possible embodiment according to any of the first aspect or second aspect, the one or more ports can be considered to comprise a port body. The port body can be provided with a head. The head can comprise an opening. The opening can be arranged for receiving and engaging with a tip of a means for administering a medical fluid, e.g., with a male luer tip of a needleless injector. The one or more ports can comprise a sealing means that is arranged to seal the opening at a closed first position, and to establish fluid flow communication through the port when brought to an open second position. The one or more ports can comprise one or more one-way valves that are arranged for allowing fluid flow from the opening conduit, and for blocking fluid flow from the conduit towards the opening.

In a possible embodiment according to any of the first aspect or second aspect, the one or more first anti-rotation means and the one or more second anti-rotation means can be arranged for snap-fit engagement with one another, thereby providing a haptic response at assembling and disassembling of the respective manifold.

An embodiment of two or more connectors according to the first aspect, or an embodiment of one or more first connectors and one or more second connectors according to the second aspect can comprise two or more first anti-rotation means and/or two or more second anti-rotation means, that are distributed around the first axis. This provides orientational flexibility regarding ports around the first axis, on consecutive or alternating arrangement of connectors according to any of the first or second aspects at constituting a respective manifold according to the present disclosure.

BRIEF DESCRIPTION OF THE DRAWINGS

FIG. 7a is side view of a connector body for a further exemplary embodiment of connector according to the present disclosure.

FIG. 7b is an axial section view of the body from FIG. 7a.

FIG. 7c is exploded view of a connector with the body from FIG. 7a.

FIG. 7d is side view of the connector from FIG. 7c.

FIG. 7e is axial section of the connector from FIG. 7d.

FIG. 7f is perspective view showing an exemplary number of connectors aligned in order to prepare for engaging to one another to form a manifold according to the first aspect.

FIG. 7g is perspective view based on FIG. 7f, where the connectors are now engaged to one another, thereby forming a manifold according to the first aspect.

FIG. 7h is perspective view where the inlet of a connector and outlet of another connector in the manifold from FIG. 7g are coupled with respective medical tubings.

FIG. 7i is side view of the manifold from FIG. 7h when in use.

FIG. 8a is side view of a connector body for a further exemplary connector embodiment according to the present disclosure, that can be considered within the second aspect.

FIG. 8b is axial section of the connector body from FIG. 8a.

FIG. 8c is exploded view of a connector provided with the connector body from 8a.

FIG. 8c1 is perspective view of the connector from FIG. 8c.

FIG. 8d is side view of the connector from FIG. 8c.

FIG. 8e is axial section of the connector based on FIG. 8d.

FIG. 9a is side view of another connector body to be employed in a connector according to the first aspect.

FIG. 9b is a section of the connector body from FIG. 9a.

FIG. 9c is exploded view of a connector with the connector body from FIG. 9a.

FIG. 9d is side view of the connector from FIG. 9c.

FIG. 9e is axial section of the connector from FIG. 9d along the first axis.

FIG. 10a is side view of a connector body for an exemplary first connector to be employed in a manifold according to a second aspect.

FIG. 10b is a section of the body from FIG. 10a along the first axis.

FIG. 10c is exploded view of a connector with the body from FIG. 10a.

FIG. 10d is side view of the connector from FIG. 10c.

FIG. 10e is axial section of the connector from FIG. 10d along the first axis.

FIG. 10h is perspective view of the manifold from FIG. 10g, attached on a medical fluid supply line.

FIG. 10i shows an exemplary use of the manifold from FIG. 10h.

FIG. 11a is side view of a connector body for an exemplary first connector to be employed in a manifold according to the second aspect.

FIG. 11b is a section of the connector body from FIG. 11a.

FIG. 11c is exploded view of a first connector according to the second aspect, with the connector body from FIG. 11a.

FIG. 11d is side view of the first connector from FIG. 11c.

FIG. 11e is axial section of the first connector from FIG. 11d.

FIG. 12a is side view of a connector body for being employed in a second connector according to the second aspect.

FIG. 12b is a section of the connector body from FIG. 12a along the first axis.

FIG. 12c is exploded view of a second connector according to the second aspect, with the body from FIG. 12a.

FIG. 12d is side view of the second connector from FIG. 12c.

FIG. 12e is axial section of the second connector from FIG. 12d.

FIG. 13a is a partially exploded side view in which first connectors and second connector(s), such as those exemplified in FIG. 11c and FIG. 12c, are aligned in an alternating fashion for engaging to one another, in order to prepare an embodiment of a manifold according to the second aspect.

FIG. 13b is perspective view of a manifold based on FIG. 13a, respective ends of two connectors that are distal to one another being engaged with respective medical tubing.

FIG. 14a is side view of a manifold according to the second aspect, in which both ends (that is, both of the first end and second end) of a first connector such as the one exemplified in FIG. 11d is engaged with respective second connectors such as the one exemplified in FIG. 12d.

FIG. 14b is side view of a manifold based on FIG. 14a, in which a further first connector as exemplified in FIG. 11d is added, thereby increasing the number of ports in the manifold.

FIG. 14c is side view of a manifold according to the second aspect, as an alternative arrangement to that shown in FIG. 14a. Here, both ends of a second connector such as the one exemplified in FIG. 12d is engaged with respective first connectors such as the one exemplified in FIG. 11d.

FIG. 15a shows an exemplary connector body provided with means for snap-fit engagement, for use in one or more connectors according to the first aspect, or in one or more first connectors and/or one or more second connectors according to the second aspect.

FIG. 15b is axial section of the connector body from FIG. 15a.

FIG. 15c is side view of an exemplary connector provided with the connector body shown in FIG. 15a, and with one or more (here, two) ports.

FIG. 15d is axial section of the connector from FIG. 15c.

FIG. 15e shows alignment of two or more (here: four) connectors that are exemplified in FIG. 15c for engaging to one another, as a preparation to form a manifold according to the first aspect.

FIG. 15f exemplifies a manifold that is obtained after engaging the connectors shown in FIG. 15e to one another.

FIG. 15g is perspective view of the manifold from FIG. 15f, prepared for use by attaching medical tubings to respective connectors that are distally arranged with regard to one another.

FIG. 15h is side view showing the manifold from FIG. 15g when in an exemplary use.

FIG. 16a exemplifies a use by medical fluid administration through one or more (here: two) ports in a connector (here: the one that is exemplified in FIG. 7a) according to the present disclosure.

FIG. 16b is axial section based on FIG. 16a.

FIG. 16c exemplifies a use of an exemplary manifold that includes two or more (here: four) connectors as shown in FIG. 16a.

FIG. 16d is axial section based on FIG. 16c.

REFERENCE SIGNS

- 10 connector body
- 11 first end
- 12 second end
- 13 sleeve
- 20 port body
- 21 head
- 22 inner cavity
- 23 opening
- 24 sealing means/sealing body
- 25 one-way valve
- 26 port
- 30 tip
- 31 tubing
- 100 connector
- 101 first connector
- 102 second connector
- 121 first anti-rotation means (notch)
- 122 second anti-rotation means (indentation)
- 151 manifold
- 152 manifold
- A1 first axis
- A2 valve axis
- C conduit

DETAILED DESCRIPTION

With reference to the appended drawings, the present application proposes a manifold (151) comprising two or more connectors (100) that are engaged to one another. The connectors (100) and thus, the manifold (151) are for communication of one or more medical fluids, for instance, to a blood stream catheter or a medical tubing (31) that can be connected to such catheter. Within the present context, a medical fluid can be a bodily fluid such as blood or any liquid that can be administered to a mammal. Yet, medically used gases, for example, air can also be considered as a medical fluid within the present context.

Figures 1, 2:
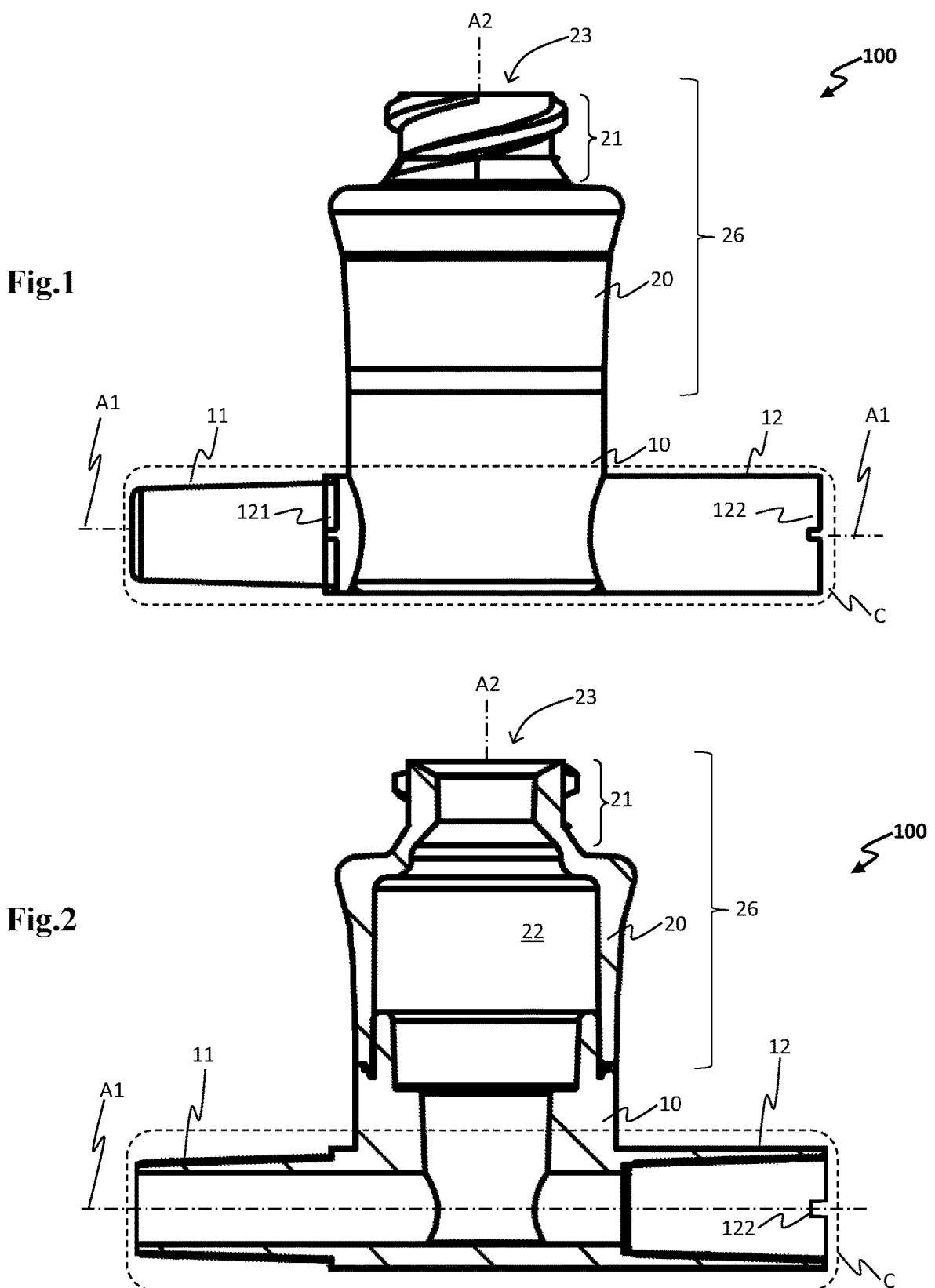
FIG. 1 is side view of an exemplary connector embodiment according to a first aspect of the present disclosure.
FIG. 2 is section view of the connector from FIG. 1.

FIG. 1 shows a side view of an exemplary connector (100) embodiment according to the present disclosure. FIG. 2 is section view of the connector (100) from FIG. 1. Referring to FIG. 1 and FIG. 2. The connector (100) comprises a connector body (10).

Referring to FIG. 2, the connector body (10) can be considered to define an inner volume as a conduit (C) for a stream of medical fluid to flow along a flow direction between a first end (11) and second end (12) of the connector body (10). To this end, the connector body (10) is provided with a first end (11) and a second end (12). The first end (11) and second end (12) can be also referred to as ends. Alternatively, the first end (11) and second end (12) can be referred to as inlet and outlet.

General context of the present disclosure proposes a flexible arrangement of number, positioning and orientations of sites on a manifold (150, 151, 152), at which respective tips (30) of one or more means for administering medical fluids can be engaged. The present disclosure further proposes a flexible arrangement of a size (e.g., length) and total weight of a manifold (151, 152) by enabling the constitution of the same from one, two or more connectors (100, 101, 102) that are arranged to be stackable with one another. Flexibility in size also corresponds to enabling formation of a manifold (151, 152) provided with ports (26) at a number that is just sufficient for a momentary need; thereby eliminating the weight, length and priming volume that would otherwise be brought by excessive number of valves in a prior art multiple-valve manifold. The manifolds (151, 152) according to the present disclosure provide an enhanced suitability for and comfort to minor or infant patients. The present disclosure proposes two alternative aspects that that overcome the shortcomings in the prior art. The medical manifolds proposed in the present disclosure provide easy and flexible assembling process at preparation for conduction of medical fluids through two or more valves thereon. Furthermore, the present disclosure enables manifolds (151, 152) with a minimized and/or flexibly arrangeable priming volume, weight and size; along with orientational flexibility regarding possible alignments of ports thereon. Minimized and/or flexibly arrangeable priming volume allows to use the manifolds (151) for pediatric applications.

First Aspect

Referring to FIG. 1-4, FIG. 7a-7i, FIG. 9a-10i; in a first aspect of the present disclosure, the first end (11) is in the form of a first type of a medical fluid communication interface geometry, and the second end (12) is in the form of a second type of a medical fluid communication interface geometry that is different from and geometrically complementary to said first type. Thus, size and shape of the second end (12) is arranged for engaging the second end to the first end (11) of an identical, further connector (100). The first type of medical fluid communication interface geometry can have a male fluid communication interface geometry such as a male luer slip fluid communication interface geometry (abbreviated as MLS), or a male luer lock fluid communication interface geometry (abbreviated as MLL). The second type of medical fluid communication interface geometry can be a female fluid communication interface geometry such as a female luer slip fluid communication interface geometry (abbreviated as FLS), or a female luer lock fluid communication interface geometry (abbreviated as FLL). In other words, according to the first aspect, the first end (11) can be considered to have the form of a male luer fluid communication interface geometry and the second end (12) can be considered to have the form of a female luer fluid communication interface geometry. This approach is independent from the direction of flow through the first end (11) and second end (12) when the manifold (151) is in use.

Figure 3:
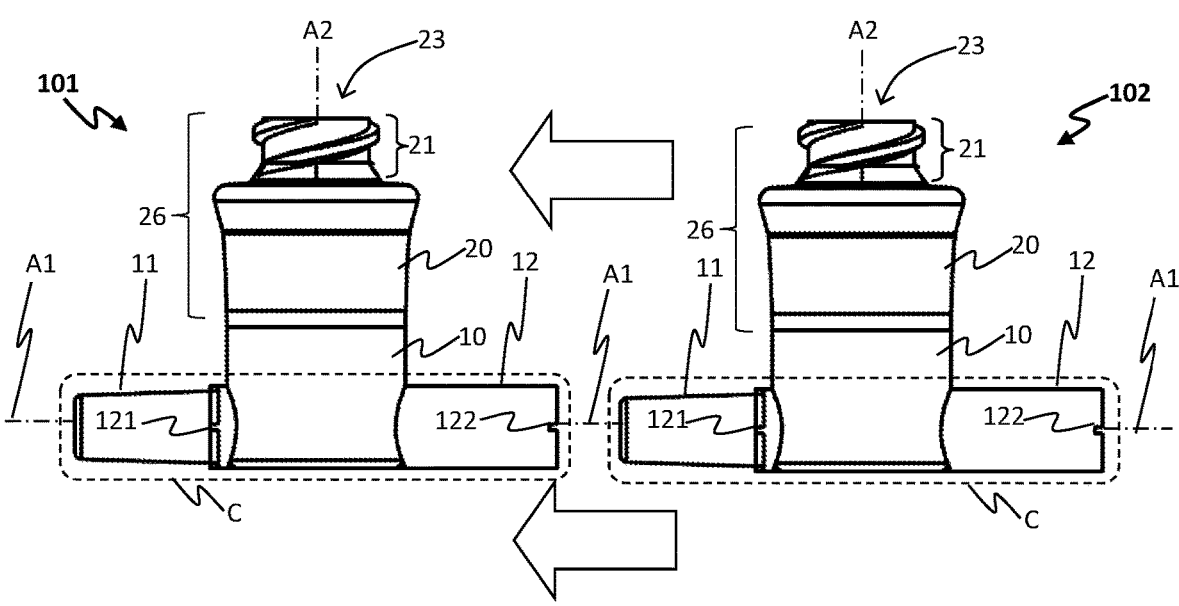
FIG. 3 is side view showing an exemplary alignment of two consecutive connectors according to the present disclosure, as a preparation for engaging to one another to form a manifold according to the first aspect.
Figure 4:
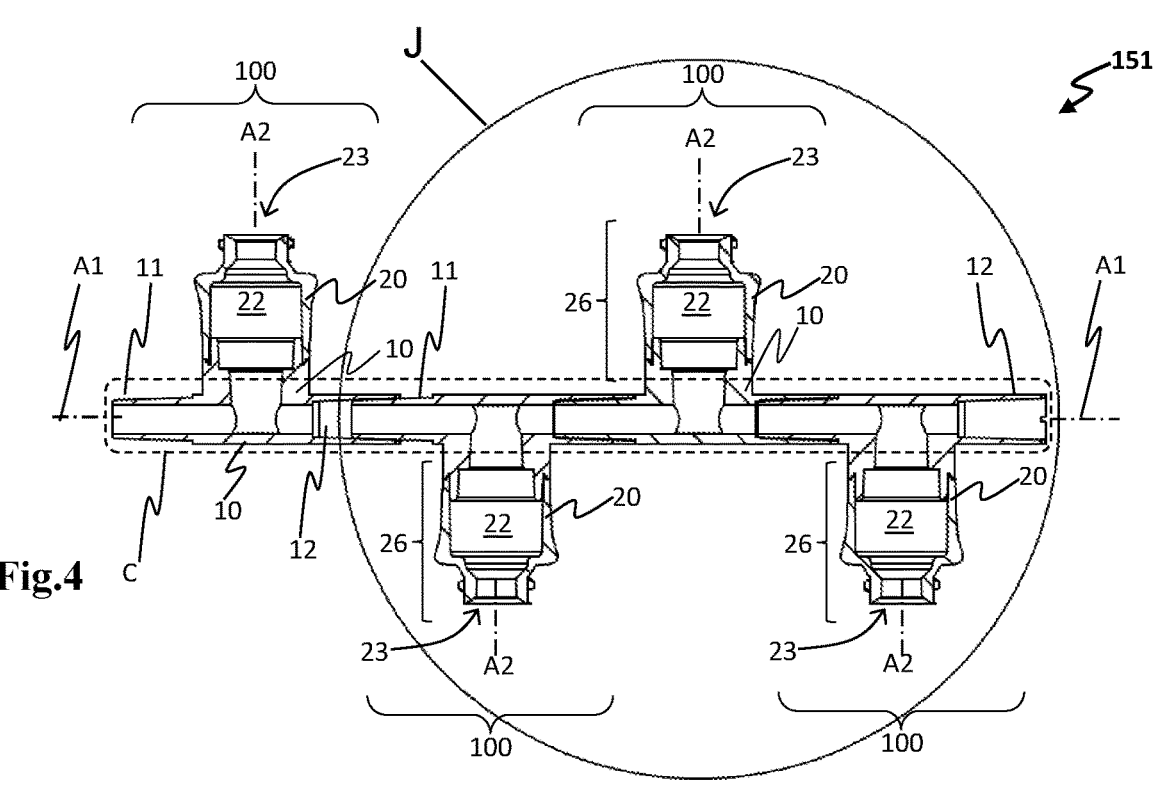
FIG. 4 is section view of a manifold that is formed by consecutively engaging a number of connectors according to the first aspect of the present disclosure, to one another.
Figure 5:
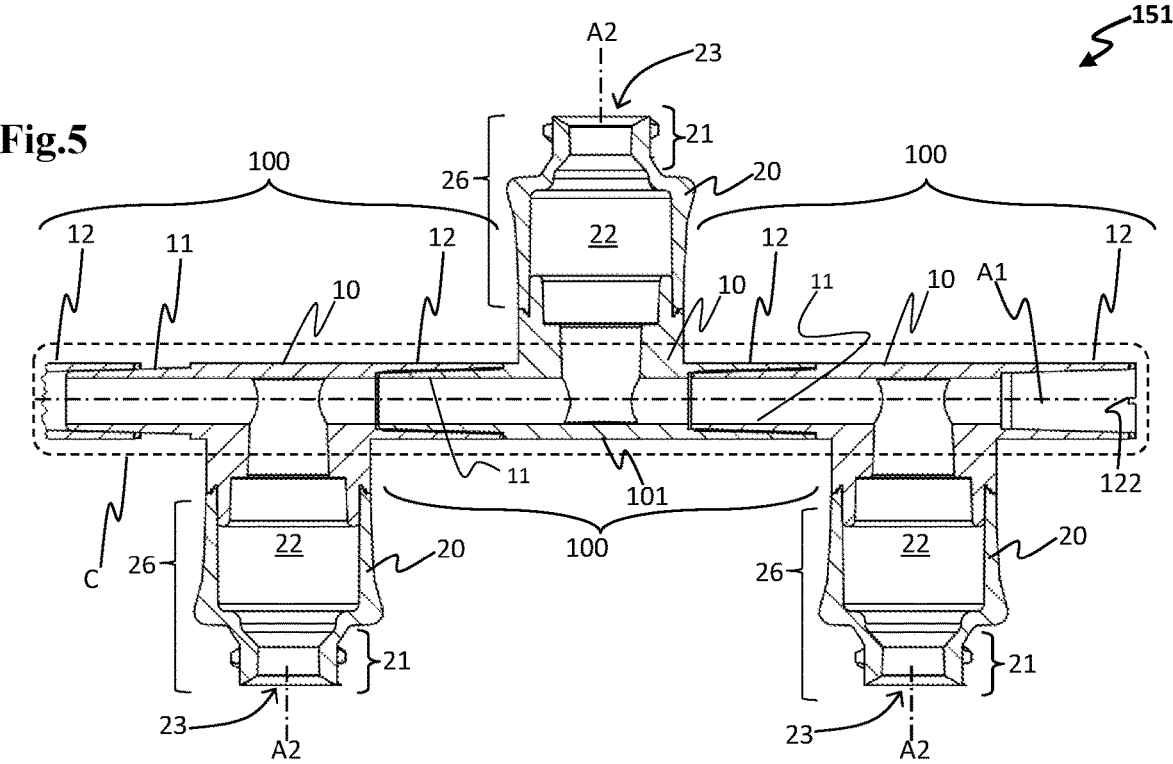
FIG. 5 is close-up view of detail-J from FIG. 4.

FIG. 3 is side view showing an exemplary alignment of two consecutive connectors (100) according to first aspect of the present disclosure, as a preparation for engaging to one another. FIG. 4 is section view of a manifold (151) that is formed from a plurality (two or more, here: four) of connectors (100) according to the first aspect of present disclosure that are consecutively engaged to one another. FIG. 5 is close-up view of detail-J from FIG. 4. With reference to FIG. 3, FIG. 4 and FIG. 5, the first aspect enables the formation of a manifold (151) by engaging the first end (11) of one or more connectors (100) to respective second end (12) of one or more further, identical connectors (100).

Accordingly, first aspect of the present application proposes that, in the manifold (151), two or more connectors (100) are stacked with one another by engaging respective first ends (11) and second ends (12) thereof. Thus the manifold (151) according to the first aspect is formed by stacking two or more connectors (100) according to the first aspect.

According to the first aspect, the term "stacking" corresponds to engaging of two or more connectors (100) to form an array, in other words, a manifold (151).

Second Aspect

Figure 6A:
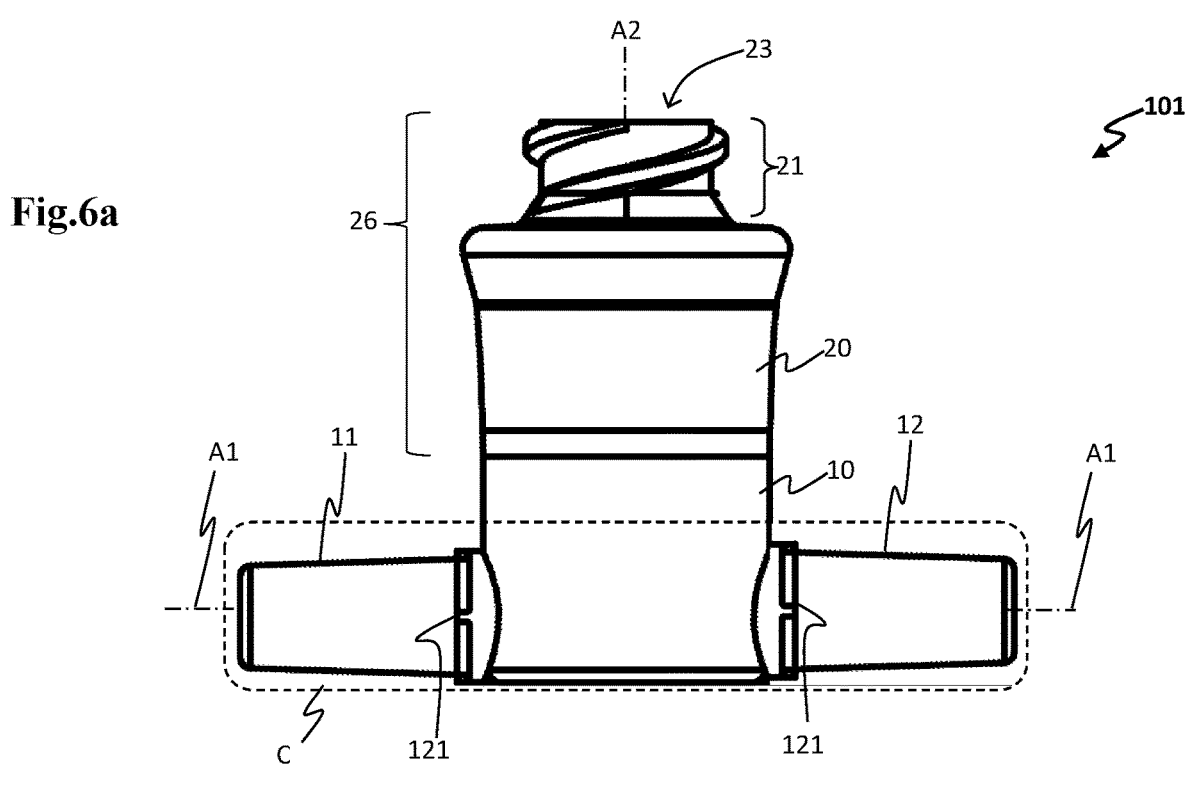
FIG. 6a is side view of an exemplary first connector according to a second aspect of the present disclosure.
Figure 6B:
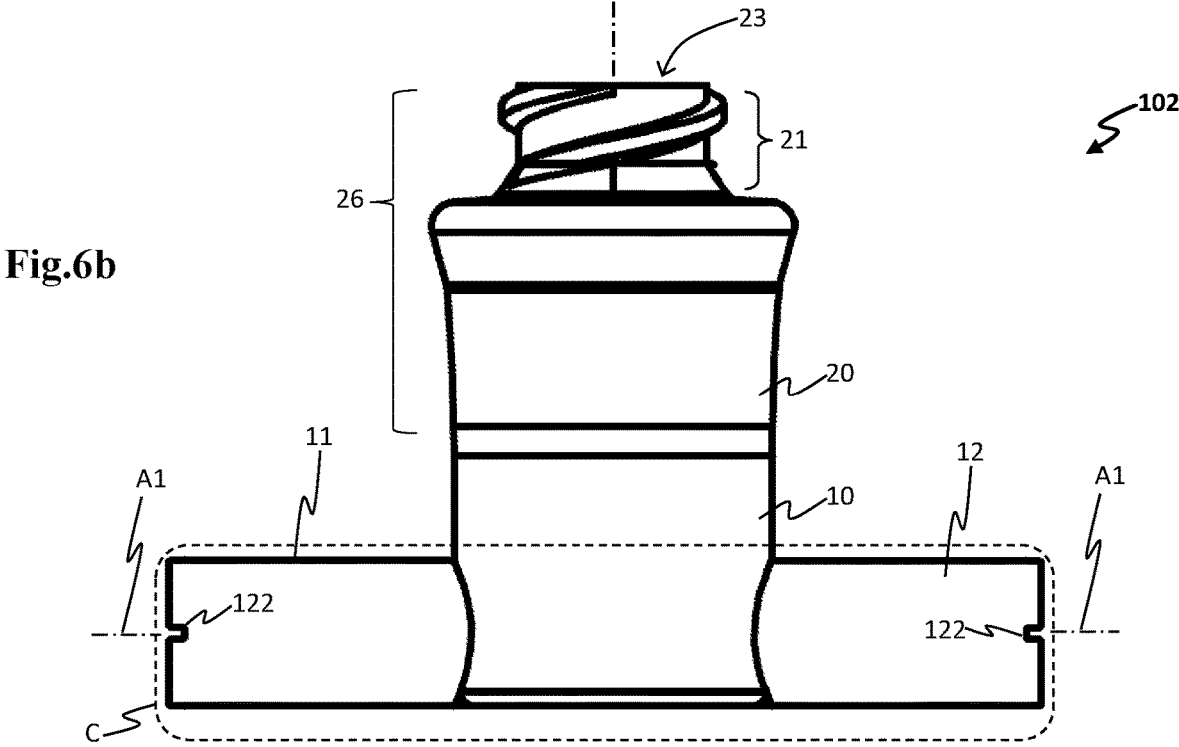
FIG. 6b is side view of an exemplary second connector according to the second aspect of the present disclosure.

In a second aspect of the present disclosure; a manifold (151) is formed from an alternated (and possibly, repeated) stacking arrangement of a first connector (101) and a second connector (102) that are arranged to engage with one another at both of first ends (11) and second ends (12) thereof. In line with the second aspect, FIG. 6a shows side view of an exemplary first connector according to the present disclosure. FIG. 6b is side view of an exemplary second connector according to the present disclosure, arranged to engage with the first connector from FIG. 6a.

According to the first aspect, the term "stacking" corresponds to engaging of one or more first connectors (101) with one or more second connectors (102) to form an array, in other words, a corresponding manifold (152).

With reference to FIG. 6a-6b, FIG. 11a-11e, FIG. 12a-12e, FIG. 13a-13b and FIG. 14a-14c; the second aspect involves a first connector (101) comprising a first end (11) and second end (12) both being of a first type of medical fluid communication interface geometry; and a second connector (102) comprising a first end (11) and second end (12) both being of a second type of medical fluid communication interface geometry that has a size and shape suitable for engaging the first end (11) or second end (12) of the first connector (101). As discussed above, the first type of medical fluid communication interface geometry can have a male fluid communication interface geometry such as a male luer slip fluid communication interface geometry (abbreviated as MLS), or a male luer lock fluid communication interface geometry (abbreviated as MLL). The second type of medical fluid communication interface geometry can be a female fluid communication interface geometry such as a female luer slip fluid communication interface geometry (abbreviated as FLS), or a female luer lock fluid communication interface geometry (abbreviated as FLL). In other words, according to the second aspect, the first end (11) and second end (12) of the first connector (101) can be considered to have the form of a male luer fluid communication interface geometry and the first end (11) and second end (12) of the second connector (102) can be considered to have the form of a female luer fluid communication interface geometry. Thus, both of the first connector (101) and second connector (102) can be considered as single-gender, arranged to cooperate with one another. This approach is independent from the direction of flow through the first end (11) and second end (12) when the manifold (151) is in use.

Figures 7A, 7B, 7C, 7D, 7E, 7F, 7G, 7H, 7I:
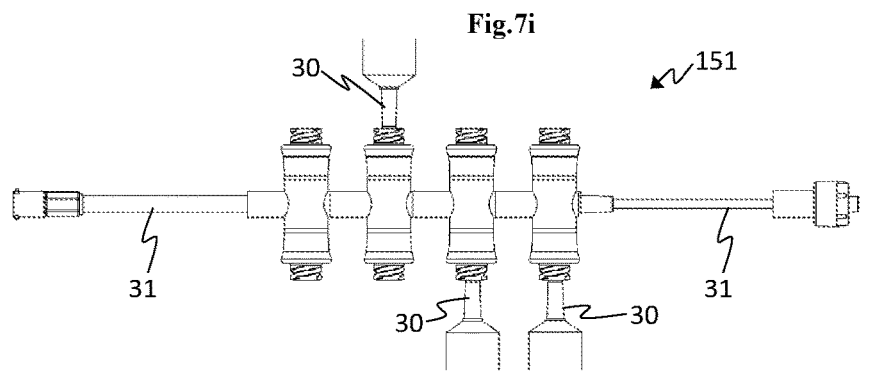

FIG. 7a is side view of the connector body (10) for a further exemplary embodiment of the connector (100) according to the first aspect present disclosure. As respectively exemplified in the form of MLS and FLS, one of the first end (11) or second end (12) can be male, and the other one thereof can be female. The connector (100) can be provided with one, two or more ports (26) (here: two). Connector (100) according to such an embodiment can be hereinafter shortly categorized as FLS-MLS. FIG. 7b is a section view of the connector body (10) from FIG. 7a along a first axis (A1). As applicable to any of the embodiments according to the present disclosure, the first axis (A1) can be considered to extend along the conduit (C) that fluidically communicates the first end (11) and second end (12). FIG. 7c is exploded view of a connector (100) with the body from FIG. 7a. FIG. 7d is side view of the connector (100) from FIG. 7c. FIG. 7e is axial section of the connector (100) from FIG. 7d along the first axis (A1). FIG. 7f is perspective view showing a plurality (two or more, here: four) of connectors (100) from FIG. 7d, that are aligned in order to prepare for engaging to one another. FIG. 7g is perspective view based on FIG. 7f, where the connectors (100) are now engaged to one another, thereby forming a manifold (151) according to the present disclosure. FIG. 7h is perspective showing a state the manifold (151) from FIG. 7g, in which the first end (11) of a connector (100) (according to the present embodiment) and second end (12) of another connector (100) at respective, distal ends of the manifold (151) are coupled with respective medical tubings (31). FIG. 7i is a side view showing a state in which the manifold (151) from FIG. 7h is in use by simultaneous or consecutive administration of medical fluids from tips (30) of respective means for administrating a medical fluid through different ports (26) in the manifold (151).

FIG. 8a is side view of the connector body (10) for a further exemplary embodiment of a connector that can be used as an end piece for being connected to a medical tubing (31). This connector embodiment can be also used as a second connector (102), to be employed in a manifold (152) according to the second aspect. In this embodiment, one of the first end (11) or second end (12) can be female (here: female luer lock fluid communication interface geometry), and the other can be arranged to engage with a medical tubing (31) (e.g., by being in the form of female luer slip fluid communication interface geometry). Again, the connector can be provided with one, two or more ports (26) (here: two). Such embodiment can be hereinafter categorized as FLL-TUBING or FLL-MLS. FIG. 8b is a section of the connector body (10) from FIG. 8a along the first axis (A1). FIG. 8c is exploded view of a connector (100) with the connector body (10) from FIG. 8a. FIG. 8c1 is perspective view of the connector (100) from FIG. 8c. FIG. 8d is side view of the connector (100) from FIG. 8c. FIG. 8e is axial section of the connector (100) from FIG. 8d.

FIG. 9a is side view of the connector body (10) for a further exemplary embodiment of a connector (100) according to the first aspect, to be employed in a manifold (151) embodiment according to the present disclosure. Here, one of the first end (11) or second end (12) can be male (here: male luer slip fluid communication interface geometry), and the other one of the first end (11) and second end (12) can be female (here: female luer lock fluid communication interface geometry). Again, as seen here, the connector (100) can be provided with one, two or more ports (here: two).

Such embodiment can be hereinafter categorized as FLL-MLS. FIG. 9b is an axial section of the connector body (10) from FIG. 9a. FIG. 9c is exploded view of a connector (100) with the connector body (10) from FIG. 9a. FIG. 9d is side view of the connector (100) from FIG. 9c. FIG. 9e is axial section of the connector (100) from FIG. 9d.

Figures 10F, 10G:
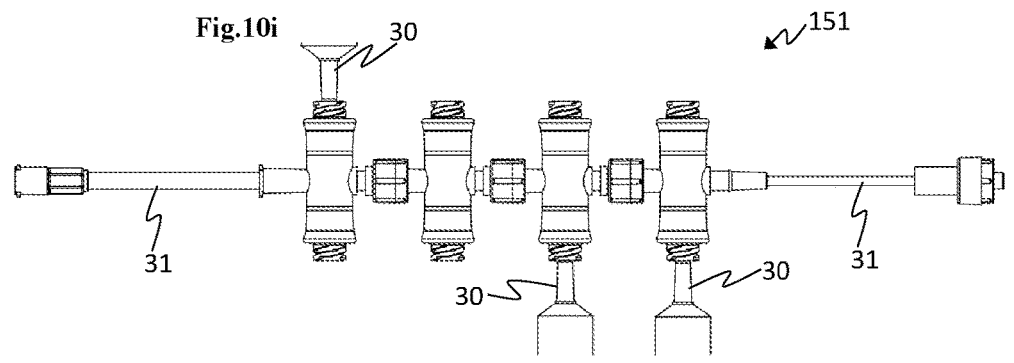
FIG. 10f is side view showing an exemplary alignment of a number of connectors from FIG. 10d, in order to prepare for formation of a manifold according to the first aspect.
FIG. 10g is manifold that is prepared on the basis of FIG. 10f.

FIG. 10a is side view of the connector body (10) for a further exemplary embodiment of a connector (100) according to the first aspect, to be employed in a manifold (151) embodiment according to the present disclosure. Here, one of the first end (11) or second end (12) can be female (here: female luer lock fluid communication interface geometry), and the other can be arranged to engage with a medical tubing (31) (e.g., by being in the form of male luer slip fluid communication interface geometry). Again, as seen here, the connector (100) can be provided with one, two or more ports (here: two). Such embodiment can be hereinafter categorized as FLL-TUBING or FLL-MLS. FIG. 10b is a section of the connector body (10) from FIG. 10a along the first axis (A1). FIG. 10c is exploded view of a connector (100) with the connector body (10) from FIG. 10a. FIG. 10d is side view of the connector (100) from FIG. 10c. FIG. 10e is axial section of the connector (100) from FIG. 10d along the first axis (A1). FIG. 10f is perspective view showing a plurality (two or more, here: four) of connectors (100) aligned in order to prepare for engaging to one another. FIG. 10g is perspective view based on FIG. 10f, where the connectors (100) are now engaged to one another, thereby forming a manifold (151) according to the present disclosure. Referring to FIG. 10c to FIG. 10g, a connector (100) according to the present disclosure can be provided with a sleeve (13) that can be attachable to a male luer slip fluid communication interface geometry (MLS) type first end (11) or second end (12) (here: to the first end 11), e.g., with a snap-fit arrangement; thereby converting the respective first end (11) or second end (12) into a male luer lock fluid communication interface geometry (MLL). FIG. 10h is perspective view where the first end (11) of a connector (100) and outlet of another, connectors (100) at two distal ends of the manifold (151) from FIG. 10g are coupled with respective medical tubings (31). FIG. 10i is side view in which the manifold (151) from FIG. 10h is in use by simultaneous or consecutively engaged tips (30) of respective means for administration of medical fluids, through different ports (26) in the manifold (151).

FIG. 11a is side view of the connector body (10) for a further exemplary embodiment of a connector (here: first connector 101) according to the second aspect, to be employed in a manifold (151) embodiment according to the present disclosure. Here, both of the first end (11) and second end (12) are male (e.g., male luer fluid communication interface geometry, here: female luer slip fluid communication interface geometry); arranged to engage with an alternate connector (that is, second connector 102) according to the second aspect, in which both of the inlet and outlet can be female (e.g., female luer fluid communication interface geometry, such as female luer lock od female luer slip fluid communication interface geometry). Again, as exemplified here, any embodiment of the first connector (101) can be provided with one, two or more ports (26) (here: two). Such embodiment of the first connector (101) can be hereinafter categorized as ML-ML or MLS-MLS. FIG. 11b is a section of the connector body (10) from FIG. 11a along the first axis A1).

FIG. 11c is exploded view of a first connector (101) with the connector body (10) from FIG. 11a. As visually exemplified here, first end (11) and/or second end (12) of the first connector (101) can be further provided with one or more threaded sleeves (13) (e.g., by respective snap-fit connections) for circumferentially engaging with respective female luer lock fluid communication interface geometry (FLL) type first end (11) and/or second end (12) of a second connector (102). The threaded sleeves (13) enable categorizing such first connector (101) as MLL-MLL; and without the threaded sleeves, the first connector (101) can be categorized as ML-ML or MLS-MLS. FIG. 11d is side view of the first connector (101) from FIG. 11c. FIG. 11e is axial section of the first connector (101) from FIG. 11d.

FIG. 12a is side view of the connector body (10) for a further exemplary embodiment of a connector (here: second connector 102) according to the second aspect, to be employed in a manifold (151) embodiment according to the present disclosure. Here, both of the first end (11) and second end (12) are female (e.g., female luer fluid communication interface geometry, here: female luer lock fluid communication interface geometry); arranged to engage with a first connector (101) (as visually exemplified in FIG. 6a, and FIG. 11c to FIG. 11e) in which both of the first end (11) and second end (12) can be male (e.g., male luer fluid communication interface geometry, such as male luer lock fluid communication interface geometry). Again, any embodiment of the second connector (102) can be provided with one, two or more ports (26) (here: two). The second connector (102) can be hereinafter categorized as FL-FL or FLL-FLL.

FIG. 12b is a section of the connector body (10) from FIG. 12a along the first axis (A1). FIG. 12c is exploded view of a second connector (102) with the connector body (10) from FIG. 12a.

FIG. 12d is side view of the second connector (102) from FIG. 12c. FIG. 12e is axial section of the second connector (102) from FIG. 12d.

FIG. 13a is a partially exploded side view in which one or more (here: two) first connectors (101) and one or more (here: one) second connectors (102), that are respectively exemplified in FIG. 11c and FIG. 12c, are aligned in an alternating fashion for engaging to one another, in order to prepare an example to manifold (152) according to second aspect of the present disclosure. FIG. 13b is perspective view of the manifold (152) based on FIG. 13a, at a state in which a first end (11) of a connector and a second end (12) of another connector that is distal with regard to the latter connector (here: both being first connectors 101) are engaged with respective medical tubing (31).

Respective uses of a manifold (151) according to the first aspect and a manifold (152) according to the second aspect of the present disclosure, can be considered comparable or same with each other. A difference between the first aspect and second aspect can be described as follows:

as visually exemplified in FIG. 3, FIG. 7f and FIG. 10f; formation of a manifold (151) according to the first aspect can be performed by consecutively engaging two or more connectors (100) according to the first aspect, by introduction of a first end (11) of a connector (100) to the second end (12) of an adjacent, consecutive connector (100) that can be identical to the latter connector (100);

as visually exemplified in FIG. 13a; formation of a manifold (152) according to the second aspect can be performed by alternatingly engaging one or more first connectors (101) with one or more second connectors (102) according to the second aspect, by engagement of the first connector (101) to the second connector (102) at first end (11) of one and cooperating second end (12) of the other.

FIG. 14a is side view of a manifold (152) according to second aspect, in which the first end (11) and second end (12) (thus, both male ends; here: male luer fluid communication interface geometry ends) of a first connector (101) (here: based on the example shown in FIG. 11d) is engaged with respective second connectors (102) such as the one exemplified in FIG. 12d. Thus, different single-gender connectors (here: one first connector 101 and two second connectors 102) according to second aspect within the scope of the present disclosure, are combined and stacked to one another in an alternating fashion, to form of an array that corresponds to a manifold (152) according to second aspect of the present disclosure.

FIG. 14b is side view of a manifold (152) based on FIG. 14a, in which a further first connector (101) as exemplified in FIG. 11d is added to an end (that is, to a female end, here: female luer fluid communication interface geometry end), thereby increasing the number of available ports (26) in the manifold (152).

FIG. 14c is side view of a manifold (152) as an alternative arrangement to that what is shown in FIG. 14a. Here, both female ends (first end 11 and second end 12) of a second connector (102) such as the one which is exemplified in FIG. 12d, are engaged with respective male ends (first end 11 or second end 12) of two first connectors (101) such as the one exemplified in FIG. 11d. Again, different single-gender connectors (that is, one or more first connectors 101 (here: two) and one or more second connectors 102 (here: one)) are combined and stacked to one another in an alternating fashion, to form of an array that corresponds to a manifold (152) according to the second aspect.

Referring to FIG. 1, FIG. 3, FIG. 6a-6b, FIG. 8c1 and FIG. 15a-15f, any embodiment of the connector (100), first connector (101) and second connector (102) according to the present disclosure can be provided with one or more first anti-rotation means (121) and one or more second anti-rotation means (122) arranged to geometrically match the one or more first anti-rotation means (121), for stabilizing consecutively arranged connectors against rotating around the first axis (A1). For instance, on a connector (100), first connector (101) or second connector (102) one or more of the first anti-rotation means (121) can be in the form of a notch that can for instance, extend parallel to the first axis (A1), and corresponding one or more second anti-rotation means (122) can be in the form of an indentation that is shaped and sized to cooperate with the notch geometry.

Furthermore, any embodiment of the connector (100), first connector (101) and second connector (102) can be provided two or more first anti-rotation means (121) that are distributed around the first axis (A1), and with one or more second anti-rotation means (122) that can be distributed around the first axis (A1). This enables an orientation flexibility around the first axis (A1), at consecutively engaging two connectors (100), or a first connector (101) to a second connector (102). As an alternative, any embodiment of the connector (100), first connector (101) and second connector (102) can be provided one or more first anti-rotation means (121) that are distributed around the first axis (A1), and with two or more second anti-rotation means (122) that can be distributed around the first axis (A1).

FIG. 15a shows an exemplary connector body (10) provided with one or more first anti-rotation means (121) and one or more second anti-rotation means (122) that are arranged for snap-fit engagement with one another by their size and shape. This embodiment provides a haptic and/or audible response at engaging or disengaging connectors to or from one another.

FIG. 15b is axial section of the exemplary connector body (10) from FIG. 15a. FIG. 15c is side view of an exemplary connector (100) provided with the connector body (10) shown in FIG. 15a, and with one or more (here, two) ports (26). FIG. 15d is axial section of the connector (100) from FIG. 15c. FIG. 15e shows alignment of two or more (here: four) connectors (100) that are exemplified in FIG. 15c for engaging to one another, as a preparation to form a manifold (151) within the general context of the present disclosure. FIG. 15f exemplifies a manifold (151) that is obtained after engaging the connectors (100) to one another, with reference to FIG. 15e.

FIG. 15g is perspective view of the manifold (151) from FIG. 15f, prepared for use by attaching medical tubings (31) to respective connectors (100) that are distally arranged with regard to one another. FIG. 15h is side view showing the manifold (151) from FIG. 15g when in an exemplary use.

Figures 16A, 16B, 16C, 16D:
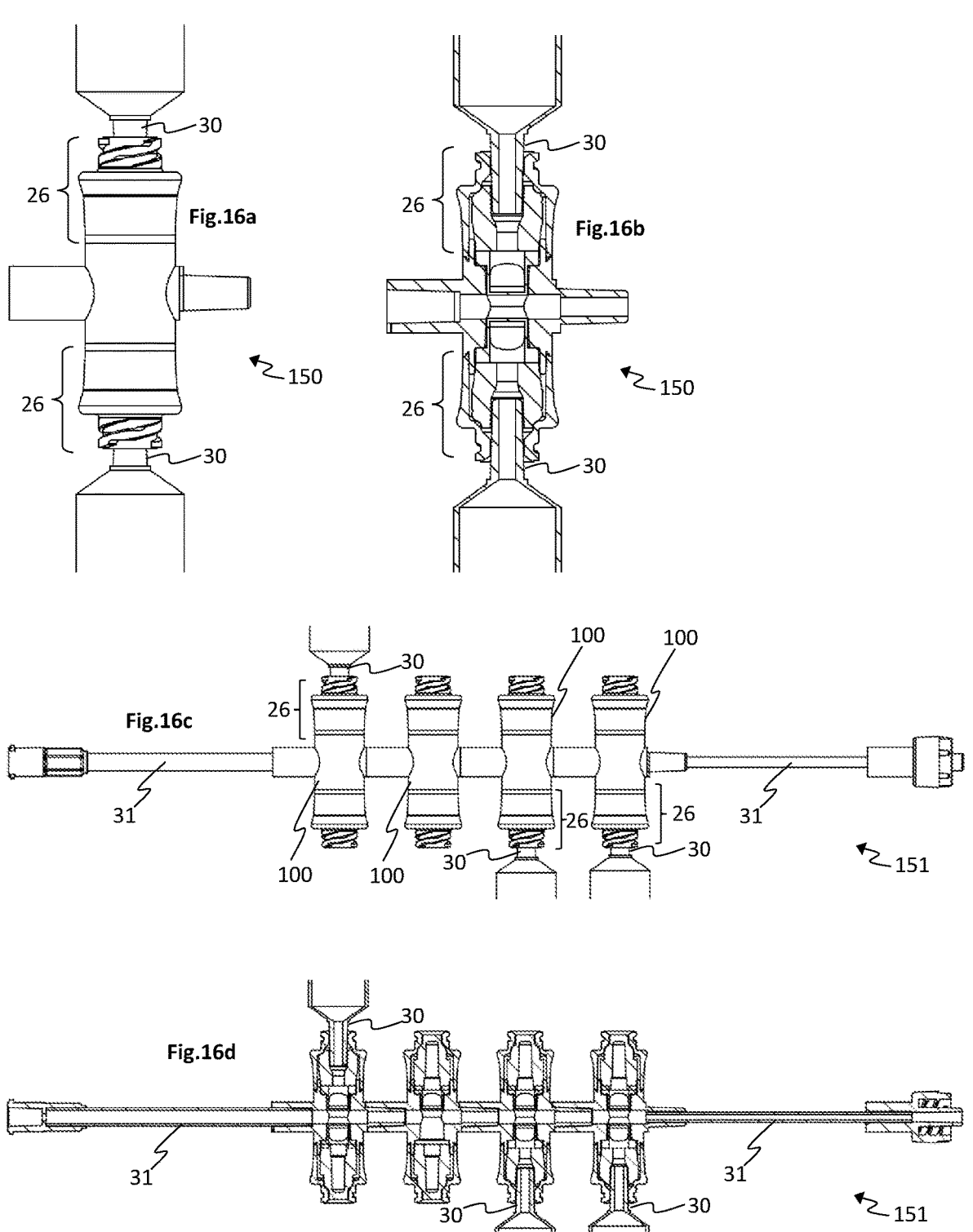

FIG. 16a exemplifies a use by medical fluid administration through one or more (here: two) ports (26) in a connector embodiment (here: exemplified over a first connector (100) of FIG. 7a) according to the present disclosure. FIG. 16b is axial section based on FIG. 16a. FIG. 16c exemplifies a use of an exemplary manifold (151) that includes two or more (here: four) connectors (100) as shown in FIG. 16a. FIG. 16d is axial section based on FIG. 16c. Possible number of ports (26) (that is: one, two or more) and their use by cooperating the same with respective tip(s) (30) are independent from a possible type of connector (100, 101, 102); that is, said possible number is independent from whether the ports (26) are provided on a connector (100) according to the first aspect to form a manifold (151) according to the first aspect, or on a first connector (101) or in a second connector (102) to form a manifold (152) according to the second aspect of the present disclosure.

Referring to visual examples provided in FIG. 7c, FIG. 8c, FIG. 9c, FIG. 10c, FIG. 11c, FIG. 12c, FIG. 16b and FIG. 16d; one or more ports (26) can be arranged between the first end (11) and the second end (12), for introduction of one or more medical fluids into the connector body (10). The one or more ports (26) can be considered to provide communication of respective medical fluids to or from a conduit (C) defined in the inner volume of the connector body (10), when a tip (30) of a means for administering a medical fluid is engaged to the port (26). As exemplified in FIG. 16a-16c, tips (30) of different means for administering medical fluid can be simultaneously engaged when a connector (100), first connector (101) or second connector (102) is in use.

The one or more ports (26) can include a port body (20), comprising a head (21) that has an opening (23). The opening (23) can be considered to be arranged for receiving and engaging with a tip (30) of the means for administering medical fluid. The tip (30) of such means for administering medical fluid can be considered to have a widely used structure, e.g., a male luer slip fluid communication interface geometry (herein abbreviated as MLS), or a male luer lock fluid communication interface geometry (herein abbreviated as MLL). So, the head (21) and opening (23) can be in the form of a corresponding, widely used structure in administering of medical fluids; that is, a female luer fluid communication interface geometry (herein abbreviated as FLS), or a female luer lock fluid communication interface geometry (herein abbreviated as FLL).

Possible inner components of one or more ports (26) that can be provided inside the port body (20) are omitted in FIG.

2, FIG. 4 and FIG. 5, in order to emphasize the cooperation-related aspects related to first opening (11) and second opening (12). Yet, as visually exemplified in FIG. 7c, FIG. 8c, FIG. 9c, FIG. 10c, FIG. 11c or FIG. 12c, in combination with FIG. 2, FIG. 4 or FIG. 5; one or more ports (26) for use in a connector (100), first connector (101) or second connector (102) can be provided with a sealing means (24) that is arranged to seal the opening (23) at a closed first position, and to establish fluid flow communication to the conduit (C) that is defined by the inner volume of the connector body (10), through the sealing means (24), when brought to an open second position. The sealing means (24) can be formed from a resilient material (e.g., silicon polymer or copolymer), that is arranged for being compressed to open when mechanically forced by the tip (30) through the opening (23) along a second axis (A2) that can be considered transverse to the first axis (A1); thereby receiving the tip (30) and taking the open second position. Furthermore, such port (26) can be provided with a one-way valve (25) arranged for allowing fluid flow from the opening (23) towards the connector body (10), and for blocking fluid flow from the connector body (10) towards the opening (23). For example, as depicted in several respective drawings appended to the present disclosure, the one-way valve (25) can be a duck bill valve.

As exemplified in FIG. 4 and FIG. 5, it can be seen that possible orientations of ports (26) in consecutive connectors (100, 101, 102) in a manifold (151 or 152) can be flexibly arranged in different radial directions around the first axis (A1).

The possible orientations can be pre-determined by design, for instance, by arranging the number and distribution of first anti-rotation means (121) and/or second anti-rotation means (122) in consecutive connectors according to the present disclosure.

The presence and number of first anti-rotation means (121), second anti-rotation means (122) and their possible arrangement for snap-fit engagement is independent from the number of ports (26), from whether the first end (11) and second end (12) are male or female, in other words, from whether they are provided in a connector (100) according to the first aspect, in a first connector (101) according to the second aspect, or in a second connector (102) according to the second aspect of the present disclosure. Likewise, a possible number, structure or inner components of ports (26) is independent from whether they are provided on a connector (100) according to the first aspect, first connector (101) according to the second aspect or second connector (102) according to the second aspect.

Male and female luer connectors within the context of the first type and second type of medical fluid communication interface geometries are well-known in the related industry, such as those defined under ISO 594 standard. Furthermore, these geometries can be considered suitable for engaging widely used medical tubings (31) with different inner or outer diameters that can be provided in accordance with respective standards. So, first end (11) or second end (12) in connectors (100), first connectors (101) and second connectors (102) can be connected to medical tubings (31) without burden when used as an end piece in a manifold (151) according to the first aspect or in a manifold (152) according to the second aspect of the present disclosure.

Within the context of the first aspect; that the two or more connectors (100) in the manifold (151) are engaged to one another should be construed in a way such that the two or more connectors (100) are produced separately from each other and stacked together when forming the respective manifold (151). Likewise, within the context of the second aspect; that the first connector(s) (101) and second connector(s) (102) in the manifold (152) are engaged to one another should be construed in a way such that the first connectors (101) and second connectors (102) are produced separately from each other and stacked together when forming the respective manifold (152).

In the manifold (151), the connectors (100) can be further adhered to one another, in order to avoid a disengagement from one another. Likewise, in the manifold (152), the first connector(s) (101) and second connector(s) (102) can be further adhered to one another, in order to avoid a disengagement from one another.

The invention claimed is:

1. A manifold comprising:

a first connector and a second connector, each of the first connector and the second connector including:

a connector body, the connector body defining a conduit and including a first end and a second end, the conduit extending through the first end and the second end and defining a first axis (A1), the first end having one of a first and a second interface geometry and the second end having one of the first and the second interface geometry that is complimentary to the interface geometry of the first end, one of the first end and the second end having at least one protrusion and the other of the first end and the second end defining at least one notch, the second end of the first connector received within the first end of the second connector to secure the first connector to the second connector, wherein the at least one protrusion of the first connector is received within the at least one notch of the second connector when the first connector is connected to the second connector in a connected position to prevent rotation of the first connector in relation to the second connector, wherein in the connected position the first connector cannot translate along the first axis (A1) towards the second connector; and a port coupled to the connector body between the first end and the second end, the port including a port body having a head defining an opening, the port body defining an inner cavity that communicates with the opening and with the conduit of the connector body, the inner cavity defining a second axis (A2) that is transverse to the first axis (A1), the head of the port body including a luer fitting to facilitate engagement with a means for administering medical fluid;

wherein each of the first end and the second end of the connector body includes a proximal end adjacent to the port and a distal end spaced from the port;

wherein the at least one protrusion is positioned radially outward of the conduits of the connector body of the first connector and the second connector on the proximal end of the first end or the second end adjacent to the port, and the at least one notch of the connector body of the first connector and the second connector is positioned on the distal end of the first end or the second end of the connector body of the first connector and the second connector spaced from the port;

wherein the first interface geometry of the first connector and the second connector is a female luer slip interface geometry and the second interface geometry of the first connector and the second connector is a male luer slip interface geometry.

2. The manifold of claim 1, wherein the at least one notch and the at least one protrusion are arranged for snap-fit engagement.

3. The manifold of claim 1, wherein the at least one notch and the at least one protrusion includes two notches and two protrusions.

4. The manifold of claim 1, wherein each of the ports of the first connector and the second connector includes a sealing body that is arranged to seal the opening at a closed first position, and to establish fluid flow communication through the port when brought to an open second position.

5. The manifold of claim 1, wherein each of the ports of the first connector and the second connector includes a one-way valve arranged for allowing fluid flow from the opening of the first connector or the second connector, and for blocking fluid flow from the conduit of the first connector or the second connector towards the opening of the first connector or the second connector.

6. A manifold comprising:

a first connector and a second connector, each of the first connector and the second connector including:

a connector body defining a conduit and including a first end and a second end, the conduit extending through the first end and the second end and defining a first axis (A1), the first end and the second end having a female or a male luer slip interface geometry, one of the first end and the second end having first anti-rotation means and the other of the first end and the second end having second anti-rotation means, the second end of the first connector received within the first end of the second connector to secure the first connector to the second connector, the first anti-rotation means received within the second anti-rotation means in snap-fit fashion when the first connector is connected to the second connector in a connected position to prevent rotation of the first connector in relation to the second connector, wherein in the connected position the first connector cannot translate along the first axis (A1) towards the second connector; and a port coupled to the connector body of the first connector and the second connector between the first end and the second end, the port including a port body having a head defining an opening, the port body defining an inner cavity that defines a second axis (A2) that is transverse to the first axis (A1) and communicates with the opening and with the conduit of the connector body;

wherein each of the first end and the second end of the connector body includes a proximal end adjacent to the port and a distal end spaced from the port;

wherein the first anti-rotation means is positioned radially outward of the conduits of the connector body of the first connector and the second connector on the proximal end of the first end or the second end adjacent to the port, and the second anti-rotation means of the connector body of the first connector and the second connector is positioned on the distal end of the first end or the second end of the connector body of the first connector and the second connector spaced from the port.

7. The manifold of claim 6, wherein the first ends of the connector bodies of the first connector and the second connector have a female luer slip interface geometry and the second ends of the first connector and the second connector have a male luer slip interface geometry.

8. The manifold of claim 6, wherein the first end and the second end of the connector body of the first connector have female luer slip interface geometries and the first end and the second end of the connector body of the second connector have male luer slip interface geometries.

9. The manifold of claim 6, wherein the first anti-rotation means includes two first anti-rotation means and the second anti-rotation means includes two second anti-rotation means.

10. The manifold of claim 6, wherein each of the ports of the first connector and the second connector includes a sealing body that is arranged to seal the opening at a closed first position, and to establish fluid flow communication through the port when brought to an open second position.

11. The manifold of claim 6, wherein each of the ports of the first connector and the second connector includes a one-way valve arranged for allowing fluid flow from the openings of the first connector and the second connector, and for blocking fluid flow from the conduits of the first connector and the second connector towards the opening of the first connector and the second connector.

12. The manifold of claim 6, wherein the first anti-rotation means moves into the second anti-rotation means in a longitudinal direction along the first axis (A1).

13. The manifold of claim 1, wherein the at least one protrusion moves into the at least one notch in a longitudinal direction along the first axis (A1).

14. The manifold of claim 6, wherein the first anti-rotation means moves into the second anti-rotation means in a longitudinal direction along the first axis (A1).

15. A manifold comprising:
a first connector and a second connector, each of the first connector and the second connector including:

a connector body defining a conduit and including a first end and a second end, the conduit extending through the first end and the second end and defining a first axis (A1), the first end and the second end having a female luer slip interface geometry or a male luer slip interface geometry;

a port coupled to the connector body between the first end and the second end, the port including a port body having a head defining an opening, the port body defining an inner cavity that defines a second axis (A2) that is transverse to the first axis (A1) and communicates with the opening and with the conduit of the connector body;

wherein each of the first end and the second end of the connector body includes a proximal end adjacent to the port and a distal end spaced from the port;

a first anti-rotation member positioned on the proximal end of the first end of the connector body and including a protrusion; and a second anti-rotation member positioned on the distal end of the second end of the connector body including a notch;

wherein the first anti-rotation member of the first connector is axially movable in a longitudinal direction along the first axis (A1) into engagement with the second anti-rotation member of the second connector to prevent rotation of the first connector in relation to the second connector.

* * * * *